United States Patent [19]
Rom et al.

[11] Patent Number: 5,746,709
[45] Date of Patent: May 5, 1998

[54] INTRAVASCULAR PUMP AND BYPASS ASSEMBLY AND METHOD FOR USING THE SAME

[75] Inventors: Paul F. Rom, Kentwood; Russell A. Corace, Grand Rapids Township, both of Mich.

[73] Assignee: Medtronic, Inc., Minneapolis, Minn.

[21] Appl. No.: 638,020

[22] Filed: Apr. 25, 1996

[51] Int. Cl.$^6$ ............................................. A61M 5/00
[52] U.S. Cl. ............................................. 604/8
[58] Field of Search ..................... 604/8, 9, 96, 19, 604/151

[56] References Cited

U.S. PATENT DOCUMENTS

| | | |
|---|---|---|
| 4,625,712 | 12/1986 | Wampler . |
| 4,704,121 | 11/1987 | Moise . |
| 4,753,221 | 6/1988 | Kensey et al. . |
| 4,779,614 | 10/1988 | Moise . |
| 4,817,586 | 4/1989 | Wampler . |
| 4,846,152 | 7/1989 | Wampler et al. . |
| 4,895,557 | 1/1990 | Moise et al. . |
| 4,906,229 | 3/1990 | Wampler . |
| 4,908,012 | 3/1990 | Moise et al. . |
| 4,944,722 | 7/1990 | Carriker et al. . |
| 4,979,937 | 12/1990 | Khorasani ............... 604/8 |
| 5,061,256 | 10/1991 | Wampler . |
| 5,092,844 | 3/1992 | Schwartz et al. . |
| 5,312,344 | 5/1994 | Grinfeld et al. . |
| 5,393,207 | 2/1995 | Maher et al. . |
| 5,425,708 | 6/1995 | Nasu . |

FOREIGN PATENT DOCUMENTS

| | | |
|---|---|---|
| 0 480 101 B1 | 5/1996 | European Pat. Off. . |
| PCT/US88/ 04295 | 12/1988 | WIPO . |
| WO 95/29716 | 11/1995 | WIPO . |

OTHER PUBLICATIONS

Anthron® Aorta Bypass Tube Product Brochure, Premiere Biomedical, undated.

"Continuous Spinal Anesthesia with a Microcatheter Technique: Preliminary Experience," by Ronald J. Hurley M.D. et al., Anesth Analg, 1990;70 pp. 97–103.

"Decending Thoracic . . . ." by Nicholas T. Kouchoukos et al., Seminars in Thoracic and Cardiovascular Surgery, vol. 5, No. 1 (Jan.), 1993: pp. 47–54.

"Distal Perfusion Methods . . . ." by M. Arisan Ergin, et al., Seminars in Thoracic and Cardiovascular Surgery, vol. 3, No. 4 (Oct.), 1991; pp. 293–299.

"Effect of Sodium . . . ." by Aurel C. Cernaianu, M.D. et al., Ann Thorac Surg, 1993;56, pp. 1035–1037.

"Experience with 1509 . . . ." by Lars G. Svensson et al., Journal of Vascular Surgery, Feb., 1993, pp. 357–370.

"Hypothermic Circulatory . . . ." by Edouard Kieffer, M.D. et al., Journal of Vascular Surgery, Mar. 1994, pp. 457–464.

"Intrathecal Perfusion . . . ," by Robert E. Maughan, M.D. et al., Ann Thorac Surg. 1992;54, pp. 818–825.

(List continued on next page.)

*Primary Examiner*—John G. Weiss
*Assistant Examiner*—John M. Black
*Attorney, Agent, or Firm*—Foley & Lardner

[57] ABSTRACT

An intravascular pump and balloon catheter assembly is shown. The assembly includes a primary catheter having a balloon provided thereon and an intravascular pump provided therein. The pump is adapted to generate a pressure differential between the inlet of the catheter and the outlet. With this structure, fluid is supplied, under pressure, to multiple arteriotomy cannulae provided at the terminal end of the assembly. The cannulae are inserted into blood vessels at appropriate points so that an occlusion or restriction in a blood vessel can be bypassed while still maintaining blood flow throughout the body.

12 Claims, 3 Drawing Sheets

OTHER PUBLICATIONS

"Pharmacologic Interventions . . . ," by A. Karim Gayumi, M.D., Ph.D. et al., The Journal of Thoracic and Cardiovascular Surgery, vol. 104, No. 2, Aug. 1992, pp. 256–261.

"Preservation of Renal . . . ," by Brent T. Allen, M.D., et al., Journal of Vascular Surgery, vol. 17, No. 5, 1993, pp. 948–959.

"Prevention of Spinal Cord . . . ," by Michael C. Mauney, M.D. et al., Ann Thorac Surg. 1995;59, pp. 245–252.

"Profound Systemic Hypothermia . . . ," Chris K. Rokkas, M.D. et al., The Journal of Thoracic and Cardiovascular Surgery, vol. 106, No. 6, 1993, pp. 1024–1035.

"Protecting the Ischemic . . . ," by Willem Wisselink, M.D. et al., Journal of Vascular Surgery, vol. 19, No. 5, 1994, pp. 788–796.

"Protection Against Ischemic Spinal Cord . . . ," by Tetsuya Ueno, M.D. et al., Journal of Vascular Surgery, vol. 19, No. 5, 1994, pp. 882–887.

"Regional Deep Hypothermia . . . ," Richard P. Salzano, Jr., M.D. et al., Ann Thorac Surg. 1994;57:65–71.

"Role of Spinal Cord Arteriography . . . ," by Edouard Kieffer, Seminars in Vascular Surgery, vol. 5, No. 3 (Sep.), 1992 pp. 141–145.

"A Second Look at the Etiology . . . ," by D. Emerick Szilagyi, M.D., Journal of Vascular Surgery, vol. 17, No. 6, 1993, pp. 1111–1113.

"Spinal Cord Injury Following Surgical . . . ," by John C. Laschinger, Seminars in Thoracic and Cardiovascular Surgery, vol. 4, No. 3 (Jul.), 1992, pp. 217–222.

"Spinal Cord Ischemic Injury: Is it Preventable?," by Nicholas T. Kouchoukos, Seminars in Thoracic and Cardiovascular Surgery, vol. 3, No. 4 (Oct.), 1991, pp. 323–328.

"Spinal Cord Protection: Development . . . ," by Tetsuya Ueno, M.D. et al., Ann thorac Surg. 1994;58, pp. 116–120.

"Spinal Cord Protection During Thoracoabdominal . . . ," by Paul A. Wojewski, The Journal of Thoracic Cardiovascular Surgery, vol. 109, No. 6, 1995, pp. 1244–1246.

"Spinal Oxygenation, Blood Supply . . . ," by Lars G. Svensson, M.D. et al., Ann Thorac Surg. 1992; 54, pp. 74–79.

"Technical Considerations in Repair . . . ," by Denton A. Cooley, Seminars in Thoracic and Cardiovascular Surgery, vol. 3, No. 4, (Oct.), 1991, pp. 329–333.

"thoracoabdominal Aneurysm Surgery," by E. Stanley Crawford et al., Seminars in Thoracic and Cardiovascular Surgery, vol. 3, No. 4 (Oct.), 1991, pp. 300–322.

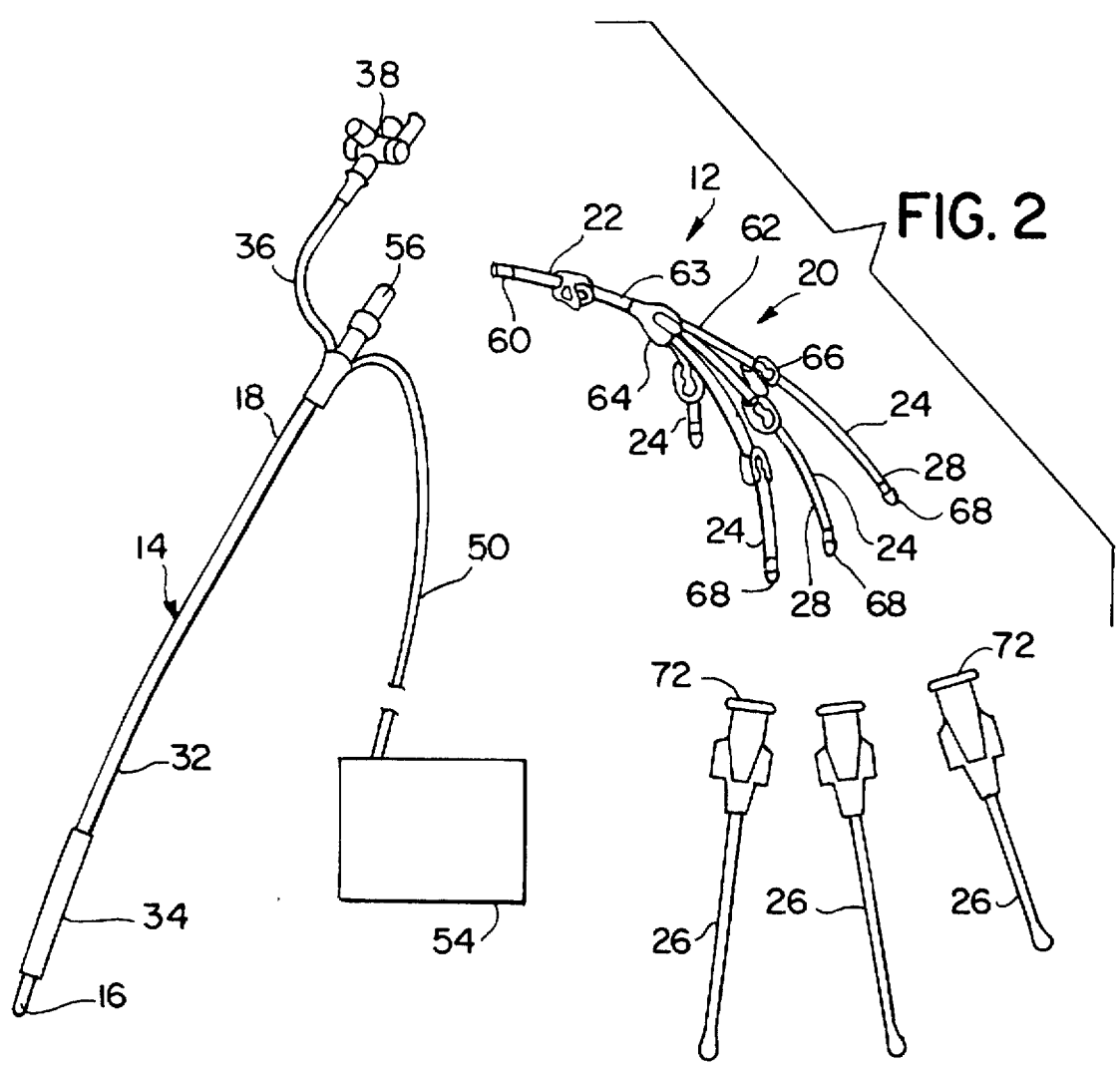
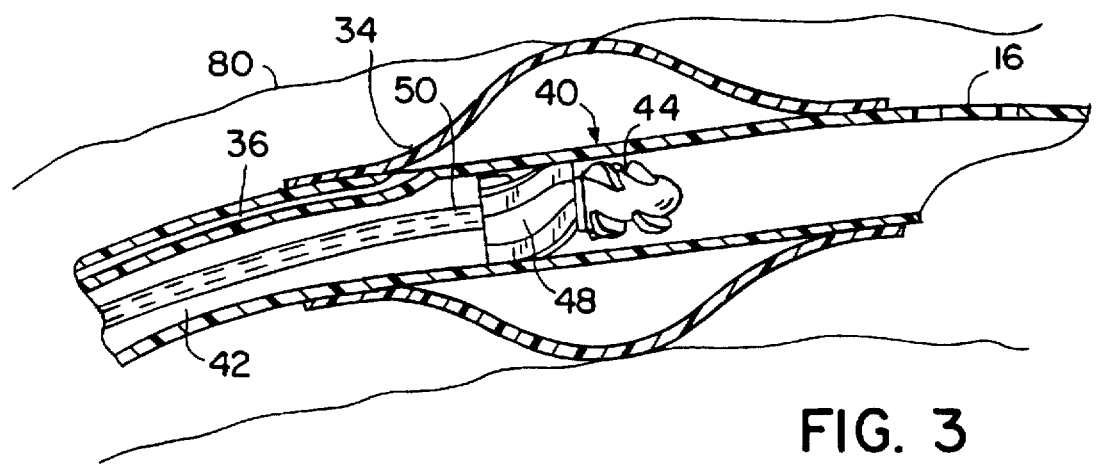

INTRAVASCULAR PUMP AND BYPASS ASSEMBLY AND METHOD FOR USING THE SAME

BACKGROUND OF THE INVENTION

1. Field of the Invention

This invention relates to a pump and catheter assembly adapted to be positioned, in part, inside a blood vessel during surgical procedures and, more particularly, to a balloon catheter having a intravascular pump provided therein, wherein the pump and catheter are used to bypass a particular portion of the vessel so that pressurized blood flow can continue throughout the body.

2. Description of the Related Art

In surgical procedures, such as the repair of an aortic aneurysm, it is necessary to cross clamp portions of the aorta while the aneurysm repair procedure is performed. Typically, the aorta is clamped both upstream and downstream from the aneurysm, thereby stopping the blood flow therethrough. While the aorta is clamped, it is necessary to continue the flow of blood to the remainder of the body. Prior means for continuing this blood flow include the process of tapping an external bypass pump into the aorta upstream from the clamp and reconnecting the pump downstream from the downstream clamp. This process has several undesireable side effects. First, the known external bypass pumps have a relatively large surface area in which the blood comes into contact. In order to prevent clotting of the blood on this large foreign surface area, significant amounts of heparin must be injected into the blood. While limited amounts of heparin are desirable during the aortic aneurysm repair procedure, avoiding clotting while using the external pump requires heparin at levels which far exceed the desired amount and is counterproductive in the overall process.

A second disadvantage of the known process is the cessation of blood flow to some of the arteries which are tapped off from the aorta intermediate the two clamps. The cessation of blood flow to the tissue serviced by these arteries can have devastating impact on the tissue. For example, paralysis has occurred in patients having aortic aneurysm repair in the area of arteries which supply blood to portions of the spine.

As is evident from above, two significant problems in the known surgical procedures for aortic aneurysm repair include the means for effectively bypassing the clamped area of the aorta during the repair procedure and supplying sufficient amounts of blood flow to arteries which tap into the aorta intermediate the clamps.

SUMMARY OF THE INVENTION

The intravascular pump and balloon catheter assembly according to the invention overcomes the problems of the prior art by providing means for bypassing the cross clamped aorta which does not require excessive amounts of heparin in the blood stream and provides means for supplying blood to the arteries intermediate the two cross clamps on the aorta.

In one aspect, the invention comprises an intravascular catheter assembly formed from a primary catheter and a plurality of subcatheters. The primary catheter comprises a body having proximal and distal ends. The distal end is adapted to be received inside a blood vessel and the proximal end is adapted to be positioned outside the blood vessel. A lumen is formed in the body along with a fluid inlet and a fluid outlet, both of which are fluidly connected to the lumen. An inflatable member, such as a balloon, is provided on the exterior surface of the body of the catheter. The balloon is selectively inflated between a retracted state and an inflated state. When the balloon is inflated in the blood vessel, it creates an obstruction in the blood vessel designed to create a positive fluid differential between the fluid outlet and the inlet. An inflation lumen is connected at one end to the inflatable member and the other end is adapted to receive fluid from a suitable source for inflating the balloon. An intravascular pump is provided in the lumen intermediate the fluid inlet and outlet. The subcatheters each have a proximal end and a distal end and a lumen provided therein. The subcatheter lumens are fluidly connected to the lumen of the primary catheter and adapted to receive fluid flowing therethrough. Each of the subcatheters is adapted to be fluidly connected to one or more blood vessels, downstream from the occlusion so that blood flow can continue through the vessels, despite the occlusion.

In a preferred embodiment, a plurality of arteriotomy cannulae are provided at the proximal end of each subcatheter. Each cannula has one end fluidly connected to the subcatheter lumen and a second end fluidly connected to the blood vessel downstream from the occlusion.

In another aspect, the invention relates to a method of providing blood flow around an aortic aneurysm comprising the steps of first providing a catheter assembly as described above. Next, the distal end of the primary catheter is inserted into the aorta, upstream from the aneurysm. At least one subcatheter is fluidly connected with the aorta, downstream from the aneurysm. The pump is actuated to begin the flow of blood through the primary catheter and subcatheters to the downstream aorta. Finally, the balloon is inflated through the application of fluid through the inflation lumen. With this structure, an aneurysm is effectively bypassed through the fluid conduit extending between the primary catheter and the subcatheter.

Preferably, subcatheters are attached to each artery extending from the aorta in which the natural blood flow is interrupted as a result of the surgical procedure to repair the aneurysm.

BRIEF DESCRIPTION OF THE DRAWINGS

The invention will now be described with reference to the drawings in which:

FIG. 2 is an exploded, elevational view of the pump and catheter assembly according to the invention;

FIG. 3 is a partial sectional view of the distal end of the intravascular pump and balloon assembly taken along lines 3—3 of FIG. 1.

DETAILED DESCRIPTION OF THE PREFERRED EMBODIMENTS

Figure 1:
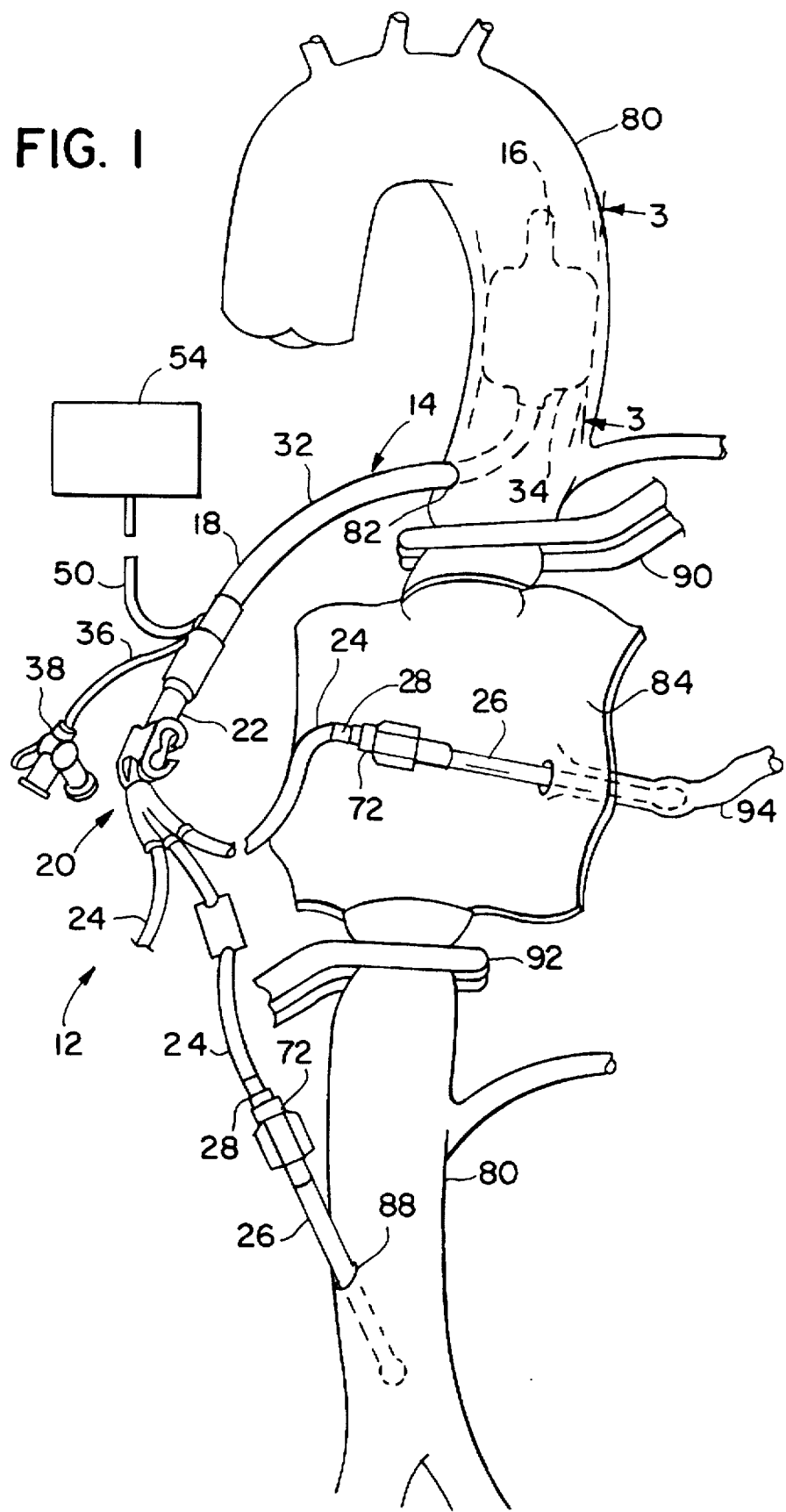
FIG. 1 is a partial, elevational view of a portion of the aorta showing use of the intravascular pump and balloon catheter assembly according to the invention.

Referring now to the drawings and to FIGS. 1–3 in particular, an intravascular pump and balloon catheter assembly 12 according to the invention is shown. The assembly 12 comprises a primary catheter 14 having a distal end 16 and a proximal end 18, a secondary catheter 20 having a distal end 22 and a plurality of supply catheters 24 extending therefrom, and a plurality of arteriotomy cannulae 26 selectively attached to the terminal ends 28 of the supply catheters 24. Each of these subcomponents will be described separately.

First, the primary catheter 14 comprises a catheter body 32 and an inflatable member or balloon 34 provided on the exterior surface of the catheter body. Preferably, the balloon is provided adjacent the distal end 16 of the catheter body 32. One end of an inflation lumen 36 is fluidly connected to the balloon and a conventional luer connector and stopcock valve 38 is provided on the other end thereof. The balloon 34 is adapted for selective inflation from a retracted state as seen in FIG. 2 and an expanded state as seen in FIGS. 1 and 3 through the application of fluid under pressure through the connector/valve 38 and lumen 36.

An intravascular pump 40 is also incorporated into the primary catheter 14. Preferably, the pump 40 is mounted in the lumen 42 of the catheter body 32, adjacent the distal end 16. The pump 40 is mounted a spaced distance from fluid inlets 58 provided on the distal end 16 of the catheter body 32. The pump 40 comprises a rotor 44 rotatably mounted inside the pump body 46 and a stator 48 fixedly mounted to the interior of the pump body 46. Rotation of the rotor 44 inside the pump body 46 is controlled by a suitable drive mechanism 54 provided a spaced distance from the pump. The rotor 44 is interconnected to the drive mechanism 54 by a drive cable 50 extending proximally therefrom. Preferably, the drive cable 50 is provided inside a cable sheath formed from a compatible material. Examples of acceptable structures for the intravascular blood pump 40 are seen in PCT Patent Application WO 89/05164, U.S. Pat. No. 4,846,152 and U.S. Pat. No. 4,944,722, each of which are expressly incorporated herein by reference. One example of an acceptable drive mechanism is seen in U.S. Pat. No. 4,895,557 which is expressly incorporated herein by reference.

The proximal end 18 of the primary catheter 14 has a conventional connector 56 provided thereon. The connector 56 is adapted to telescopically receive a complementary connector 60 provided on the distal end 22 of the secondary catheter 20. The connectors 56, 60 cooperate to establish fluid communication between the lumen 42 of the primary catheter 14 and the lumen of the secondary catheter 20. The secondary catheter is commercially available from the DLP Division of Medtronic, Inc., located in Grand Rapids, Mich.

The secondary catheter 20 comprises a main body 62 with a lumen extending therethrough and a plurality of supply catheters 24 extending therefrom. Preferably, the main body 62 has a clamp 63 provided thereon which can be used to close the lumen and prevent the flow of fluid therethrough. A conventional interconnection 64 is provided at the junction of the main body 62 of the secondary catheter 20 and each of the supply catheters 24. The lumens of each of the supply catheters 20 are fluidly connected to the lumen of the main body 62. Preferably, each secondary catheter 20 has a clamp 66 provided on the body thereof and a conventional connector 68 provided on the terminal end thereof.

The connectors 68 of the supply catheters 24 are adapted to be telescopically received in the proximal end 72 of the arteriotomy cannulae 26. A lumen extends through the body of the cannula 26 to an aperture provided at the distal end 74. The distal end 74 is adapted to be received in a blood vessel so that blood can flow through the primary catheter 14, secondary catheter 20, supply catheter 24 and cannula 26. The cannulae 26 are commercially available from the DLP Division of Medtronic, Inc. located in Grand Rapids, Mich.

One application of the intravascular pump and balloon catheter assembly 12 according to the invention is seen in FIG. 1. In this embodiment, the assembly 12 is adapted for use in repairing an aortic aneurysm. The process is performed by first inserting the distal end 16 of the primary catheter 14 into the aorta 80 through an incision 82 provided upstream from the affected aortic tissue 84. The distal end 16 of the catheter is inserted with the balloon 34 in the retracted state. Next, one or more of the cannulae 26 are inserted into the aorta 80 downstream from the affected tissue 84 through an appropriate incision 88. A suitable fluid is supplied through the inflation lumen 36 to inflate the balloon until it fully occludes the fluid flow through the aorta 80. While it is preferred that the balloon fully occludes the fluid flow, this condition is not necessary. The balloon could be adapted to only partially occlude the aorta 80. Simultaneously, or prior to the inflation, the pump 40 is activated by the drive mechanism 54. Fluid is drawn into the distal end 16 of the primary catheter 14 and flows to the secondary catheter 20 and the fluidly connected cannula 26. Once these fluid interconnections are established and the pump 40 is activated, the pump 40 creates an effective bypass of the affected tissue 84 of the aorta 80. With the bypass in place, the aorta can be cross clamped both upstream and downstream of the affected tissue 84 by a pair of clamps 90, 92. Next, the affected tissue 84 of the aorta 80 can be opened so that the necessary repair of the aneurysm can be performed.

Depending upon the location of the affected tissue, the fluid flow from the aorta could be terminated for one or more arteries. As seen in FIG. 1, an artery 94 fluidly connects to the aorta 80 intermediate the clamps 90, 92. In order to continue the flow of blood to the artery 94 and the tissue serviced by the artery, one of the cannula 26 is inserted into the artery 94 and the appropriate clamp 66 is opened. With this arrangement, oxygenated blood is drawn through the intravascular pump and supplied to the aorta 80 downstream from the clamp and to arteries intermediate the clamps 90, 92 on the aorta. The arteriotomy cannulae 26 can also be tapped into other arteries requiring an enhanced fluid flow or arteries 96, as seen in FIG. 1, intermediate the balloon 34 and the upstream aortic clamp 90 in which the natural blood flow is disrupted.

Using this structure, bypass for the cross clamped aorta is achieved while simultaneously providing means for supplying pressurized blood flow to other affected arteries. Use of the intravascular pump is ideal for patients having a weakened heart or which are otherwise prevented from generating strong blood flow. The pump will create a significant pressure differential between the inlet of the pump and the outlet so that all arteries fluidly connected to the outlet of the pump will be provided with an adequate supply of blood.

Experimentation has shown that use of the intravascular pump according to the invention reduces the required amount of anticoagulant drugs such as heparin. It is believed that this beneficial effect is the result of the reduced surface area which the blood contacts during the bypass procedure. Regardless of the cause, the benefit is substantial because surgeons can now reduce the amount of heparin introduced into the bloodstream during an aneurysm repair procedure and thereby speed recovery from the surgical procedure.

Figure 4:
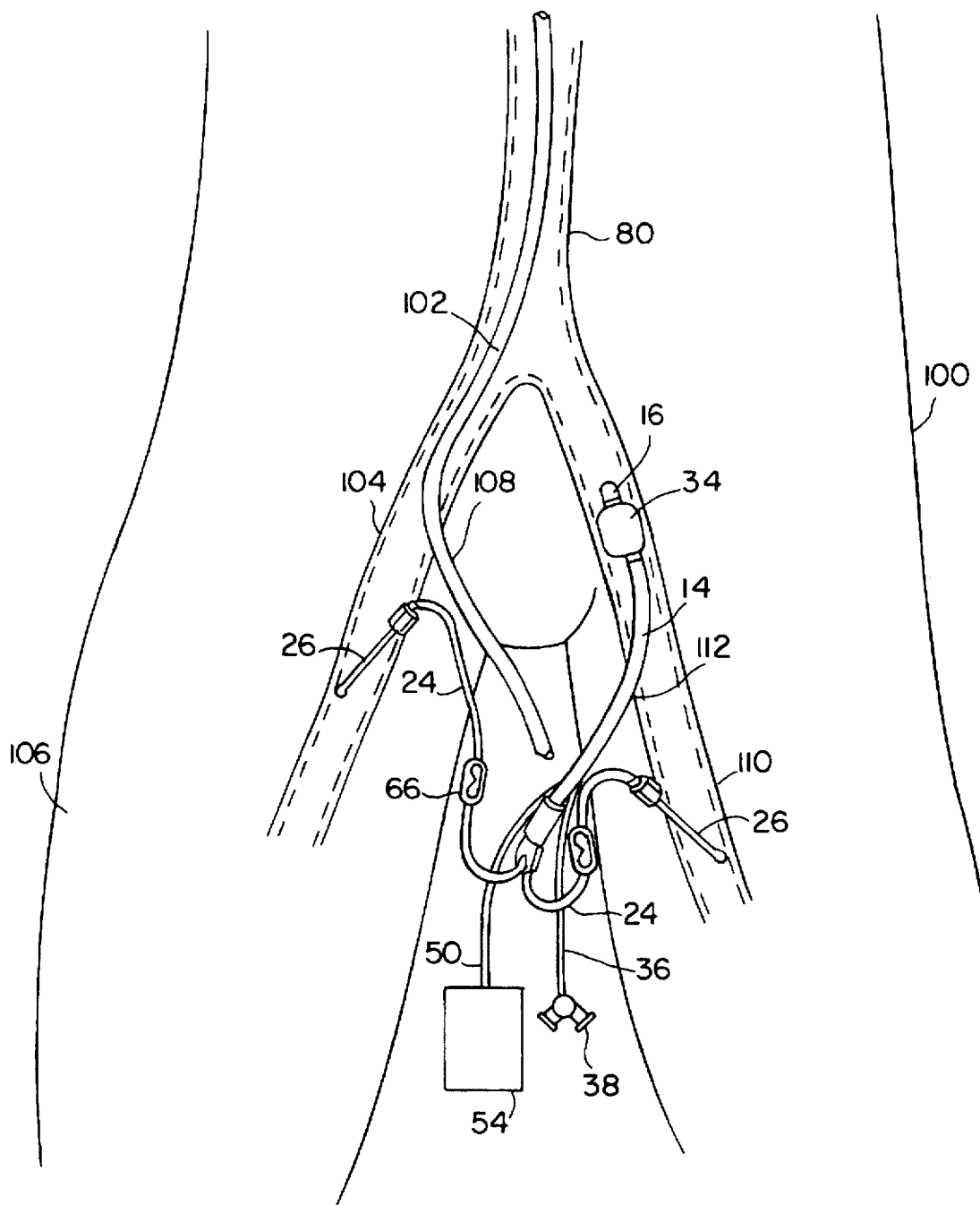
FIG. 4 is a partial elevational view of the legs and torso of a patient showing an alternative application for the intravascular pump and balloon catheter assembly according to the invention.

FIG. 4 shows an alternative application of the intravascular pump and balloon catheter assembly 12 according to the invention. In this application, a patient 100 has a catheter 102 inserted into the right femoral artery 104. The catheter 102 can be used for a host of different conventional procedures. One problem experienced by patients having devices, such as the catheter 102, inserted into the femoral artery is the sufficiency of the blood flow to the right leg 106, downstream from the insertion point 108 of the catheter 102.

The intravascular pump and balloon catheter assembly 12 according to the invention can be used to divert some of the blood flow from the left femoral artery 110 to the right femoral artery 104, downstream from the insertion point 108 of the catheter 102. Specifically, the distal end 16 of the catheter assembly 12 is inserted into the left femoral artery 110 through an appropriate incision 112. At least one of the arteriotomy cannulae 26 extend from the primary catheter 14 and is inserted through an appropriate incision into the right leg 106, downstream from the insertion point of the catheter 108. The pump 40 is activated so that at least a portion of the blood flowing through the left femoral artery 110 is redirected to the right femoral artery 104 downstream from the occlusion caused, in this example, by the catheter.

In the embodiment described above, the balloon is not inflated in the left femoral artery 110 so that blood flow continues therethrough. If it is necessary to inflate the balloon in order to properly position and secure the distal end 16 of the primary catheter in the artery, then some means must be provided for redirecting a portion of the blood flow to the remainder of the left leg. In the embodiment seen in FIG. 4, a second arteriotomy cannula 26 is inserted through an appropriate incision into the left artery, downstream from the incision 112. With this structure, the blood flow through the left femoral artery 110 is split between the right femoral artery 104 and the remainder of the left femoral artery 110.

An alternative to utilizing a second cannula 26 for tapping into the left femoral artery 110 would be to provide one or more apertures directly on the primary catheter body 14 so that some of the blood flow through the primary catheter is directed to the cannula 26 while a portion of the blood flows out the apertures, back into the femoral artery 110.

As is evident, the intravascular pump and balloon catheter assembly according to the invention 12 can be used in any application in which blood flow within a vessel must bypass an occlusion or restriction in flow. The incorporation of the secondary catheter and the cannulae on the primary catheter allow for a wide range of applications and adaptions of this basic structure.

Reasonable variation and modification are possible within the spirit of the foregoing specification and drawings without departing from the scope of the invention.

The embodiments for which an exclusive property or privilege is claimed are defined as follows:

1. An intravascular catheter assembly comprising:
    a primary catheter comprising:
        a body with a lumen formed therein;
        a distal end adapted to be received inside a blood vessel;
        a proximal end adapted to be positioned outside the blood vessel;
        a fluid inlet fluidly connected to the lumen;
        a fluid outlet fluidly connected to the lumen;
        an inflatable member provided on the exterior surface of the body of the catheter, the member being selectively inflated between a retracted state and an inflated state, wherein the inflatable member in the inflated state creates an occlusion in the blood vessel;
        an inflation lumen having a distal end fluidly connected to the inflatable member and a proximal end adapted to receive fluid from a suitable source; and
        an intravascular pump provided in the lumen of the catheter intermediate the fluid inlet and outlet, the pump being adapted to create a positive fluid differential between the fluid outlet and the inlet; and
    a plurality of subcatheters each having a proximal end, a distal end and a lumen formed therein, the subcatheter lumens being fluidly connected to the lumen of the primary catheter and adapted to receive fluid flowing therethrough, each of the subcatheters being adapted to be fluidly connected to one or more blood vessels downstream from the occlusion so that blood flow can continue through the blood vessels, despite the occlusion.

2. An intravascular catheter assembly according to claim 1 and further comprising a plurality of arteriotomy intercostal cannulae provided at the proximal end of each subcatheter, each arteriotomy cannulae comprising a body with a lumen formed therein, a proximal end and a distal end, the distal end being fluidly connected to the subcatheter lumen and the proximal end being received inside a blood vessel downstream from the occlusion so that fluid being expelled from the intravascular pump is supplied downstream to blood vessels.

3. An intravascular catheter assembly according to claim 1 and further comprising a plurality of arteriotomy cannulae provided at the proximal end of each subcatheter, each cannula comprising a body with a lumen formed therein, a proximal end and a distal end, the distal end being fluidly connected to the subcatheter lumen and the proximal end being received inside a blood vessel downstream from the occlusion so that fluid being expelled from the intravascular pump is supplied downstream to blood vessels.

4. An intravascular catheter assembly according to claim 1 wherein said intravascular pump comprises a rotor rotatably mounted inside the catheter, a drive mechanism provided a spaced distance from the rotor and a drive cable having a distal end mounted to the rotor and a proximal end mounted to the drive mechanism.

5. An intravascular catheter assembly according to claim 4 and further comprising a stator securely mounted inside the catheter, adjacent the rotor.

6. A method of providing blood flow around an occlusion in a blood vessel comprising the steps of:
    providing a catheter assembly comprising:
        a primary catheter comprising:
            a body with a lumen formed therein, the body having a distal end adapted to be received inside a blood vessel, a proximal end adapted to be positioned outside the blood vessel, a fluid inlet fluidly connected to the lumen and a fluid outlet fluidly connected to the lumen;
            an inflatable member provided on the exterior surface of the body of the catheter adjacent the distal end, the member being selectively inflated between a retracted state and an inflated state, wherein the inflatable member in the inflated state creates an obstruction in the blood vessel;
            an inflation lumen having a distal end fluidly connected to the inflatable member and a proximal end adapted to receive fluid from a suitable source; and
            an intravascular pump provided in the lumen of the catheter intermediate the fluid inlet and outlet, the pump being adapted to create a positive fluid differential between the fluid outlet and the inlet; and
        at least one subcatheter having a proximal end, a distal end and a lumen formed therein, the subcatheter lumen being fluidly connected to the lumen of the primary catheter and adapted to receive fluid flowing therethrough, each of said at least one subcatheter being adapted to be fluidly connected to one or more blood vessels downstream from the occlusion so that blood flow can continue through the blood vessel, despite the occlusion;

inserting the distal end of the primary catheter into a blood vessel;

fluidly connecting the at least one subcatheter with a blood vessel downstream from the primary catheter;

actuating a the pump; and supplying fluid to the inflatable member through the inflation lumen thereby causing the inflatable member to assume the inflated state;

whereby the occlusion is effectively bypassed through the fluid conduit extending between the primary catheter and the subcatheter.

7. A method of providing blood flow around an aortic aneurysm comprising the steps of:

providing a catheter assembly comprising:

a primary catheter comprising:

a body with a lumen formed therein, the body having a distal end adapted to be received inside the aorta, a proximal end adapted to be positioned outside the aorta, a fluid inlet fluidly connected to the lumen and a fluid outlet fluidly connected to the lumen;

an inflatable member provided on the exterior surface of the body of the catheter adjacent the distal end, the member being selectively inflated between a retracted state and an inflated state;

an inflation lumen having a distal end fluidly connected to the inflatable member and a proximal end adapted to receive fluid from a suitable source; and an intravascular pump provided in the lumen of the catheter intermediate the fluid inlet and outlet, the pump being adapted to create a positive pressure differential between the fluid outlet and the inlet; and at least one subcatheter having a proximal end, a distal end and a lumen formed therein, the subcatheter lumen being fluidly connected to the lumen of the primary catheter and adapted to receive fluid flowing therethrough, said at least one subcatheter being adapted to be fluidly connected to the aorta downstream from the aneurysm so that blood flow can continue through the aorta, around the aneurysm;

inserting the distal end of the primary catheter into the aorta, upstream from the aneurysm;

fluidly connecting the at least one subcatheter with the aorta downstream from the aneurysm;

actuating the pump; and supplying fluid to the inflatable member through the inflation lumen thereby causing the inflatable member to assume the inflated state;

whereby the aneurysm is effectively bypassed through the fluid conduit extending between the primary catheter and the subcatheter.

8. A method of providing blood flow around an aortic aneurysm according to claim 7 and further comprising the steps of:

identifying any and all arteries extending from the aorta which are prevented from receiving blood flow; and fluidly connecting a second subcatheter to one of said arteries.

9. A method of providing blood flow around an aortic aneurysm according to claim 7 and further comprising the steps of:

identifying any and all arteries extending from the aorta which are prevented from receiving blood flow; and fluidly connecting a subcatheter to each of said arteries.

10. A method of providing blood flow around an aortic aneurysm according to claim 7 and further comprising the steps of:

clamping the aorta downstream from the distal end of the primary catheter, but upstream from the aneurysm; and clamping the aorta upstream from the aneurysm, but upstream from the fluid connection point of the at least one subcatheter.

11. A method of providing blood flow around an aortic aneurysm according to claim 10 and further comprising the steps of;

identifying any and all arteries extending from the aorta intermediate the two clamps which are prevented from receiving blood flow; and fluidly connecting a second subcatheter to one of said arteries.

12. A method of providing blood flow around an aortic aneurysm according to claim 11 and further comprising the step of fluidly connecting a subcatheter to each of said arteries.

* * * * *